US011466305B2

(12) United States Patent
Bae et al.

(10) Patent No.: US 11,466,305 B2
(45) Date of Patent: Oct. 11, 2022

(54) AMYOTROPHIC LATERAL SCLEROSIS DIAGNOSTIC COMPOSITION USING ACID SPHINGOMYELINASE, AND METHOD FOR DETECTING DIAGNOSTIC MARKERS

(71) Applicants: KYUNGPOOK NATIONAL UNIVERSITY INDUSTRY-ACADEMIC COOPERATION FOUNDATION, Daegu (KR); IUCF-HYU (INDUSTRY-UNIVERSITY COOPERATION FOUNDATION HANYANG UNIVERSITY), Seoul (KR); SAMSUNG LIFE PUBLIC WELFARE FOUNDATION, Seoul (KR)

(72) Inventors: Jae-Sung Bae, Daegu (KR); Hee Kyung Jin, Daegu (KR); Ju Youn Lee, Gimhae-si (KR); Seung Hyun Kim, Seoul (KR); Chang-Seok Ki, Seoul (KR)

(73) Assignees: KYUNGPOOK NATIONAL UNIVERSITY INDUSTRY-ACADEMIC COOPERATION FOUNDATION, Seoul (KR); IUCF-HYU (INDUSTRY-UNIVERSITY COOPERATION FOUNDATION HANYANG UNIVERSITY) SAMSUNG LIFE PUBLIC WELFARE FOUNDATION, Seoul (KR)

( * ) Notice: Subject to any disclaimer, the term of this patent is extended or adjusted under 35 U.S.C. 154(b) by 625 days.

(21) Appl. No.: 16/462,899

(22) PCT Filed: Oct. 20, 2017

(86) PCT No.: PCT/KR2017/011665
§ 371 (c)(1),
(2) Date: May 21, 2019

(87) PCT Pub. No.: WO2018/097485
PCT Pub. Date: May 31, 2018

(65) Prior Publication Data
US 2020/0080129 A1 Mar. 12, 2020

(30) Foreign Application Priority Data
Nov. 22, 2016 (KR) .......... 10-2016-0155859

(51) Int. Cl.
*C12Q 1/44* (2006.01)
*G01N 33/92* (2006.01)

(52) U.S. Cl.
CPC .............. *C12Q 1/44* (2013.01); *G01N 33/92* (2013.01); *G01N 2333/916* (2013.01); *G01N 2405/08* (2013.01); *G01N 2800/2878* (2013.01)

(58) Field of Classification Search
CPC ....... C12Y 301/04012; G01N 2405/08; G01N 2800/2878
See application file for complete search history.

(56) References Cited

U.S. PATENT DOCUMENTS

2016/0101070 A1\* 4/2016 Bae .................. A61P 25/28
514/44 A

FOREIGN PATENT DOCUMENTS

KR 101521117 B1 5/2015
WO WO-2014182051 A1 \* 11/2014 ........... A61K 31/133

OTHER PUBLICATIONS

Cutler ("Evidence that accumulation of Ceramides and Cholesterol esters mediates oxidative Stress-Induced Death of Motor Neurons in Amyotrophic Lateral Sclerosis" Annals of Neurology, 2002, 52, 448-457). (Year: 2002).\*
Jana et al., "Ceramide and neurodegeneration: Susceptibility of neurons and oligodendrocytes to cell damage and death", Journal of the Neurological Sciences, 2009, 278: 5-15.
Kim et al., "Genetic and functional analysis of TBK1 variants in Korean patients with sporadic amyotrophic lateral sclerosis", Neurobiology of Aging, 2016, 50: 170.e1-70.e6.
Chen et al., "Genetics of amyotrophic lateral sclerosis: an update", Molecular Neurodegeneration, 2013, 8:28, http://www.molecularneurodegeneration.com/content/8/1/28.
Dodge et al., "Gene transfer of human acid sphingomyelinase corrects neuropathology and motor deficits in a mouse model of Niemann-Pick type A disease", PNAS, 2005, 102(49): 17822-17827.

(Continued)

*Primary Examiner* — Robert J Yamasaki
*Assistant Examiner* — Charles Zoltan Constantine
(74) *Attorney, Agent, or Firm* — James S. Keddie; Bozicevic, Field & Francis LLP

(57) ABSTRACT

The present invention relates to a amyotrophic lateral sclerosis (ALS) diagnostic composition using acid sphingomyelinase (ASM), and a method for detecting diagnostic markers and, more specifically, to a method and a composition for detecting markers for ALS, the method comprising the steps of: (a) providing a sample of a subject; (b) measuring the ASM expression level or the enzyme activation level in the sample; (c) determining that a subject, of which the ASM expression level or the enzyme activation level is increased compared to that of a normal person, has ALS. According to the investigation of the present inventors, the activity of ASM, among lipids and enzymes related to the sphingolipid metabolism, is specifically increased in a sample of an ALS patient compared to that of a normal person. ASM can be used as a marker for diagnosing ALS, thereby enabling the development of a novel and effective diagnostic reagent.

5 Claims, 4 Drawing Sheets

(56) References Cited

OTHER PUBLICATIONS

Bai et al., "Role of acid sphingomyelinase bioactivity in human CD4+ T-cell activation and immune responses", Cell Death & Disease, 2015, 6(7): e1828-e1828.

Muhle et al., "Characterization of Acid Sphingomyelinase Activity in Human Cerebrospinal Fluid", PLOS One, 2013, 8 (5): e62912.

Robelin et al., "Blood Biomarkers for Amyotrophic Lateral Sclerosis: Myth or Reality?", BioMed Research International, 2014, 2014(1): 1-11.

Rousson et al., "Preparation of an anti-acid sphingomyelinase monoclonal antibody for the quantitative determination and polypeptide analysis of lysosomal sphingomyelinase in fibroblasts from normal and Niemann-Pick type A patients", Journal of Immunological Methods, 1993, 160(2): 199-206.

Schuchman et al., "Human Acid Sphingomyelinase. Isolation, nucleotide sequence, and expression of the full-length and alternatively spliced cDNAs", The Journal of Biological Chemistry, 1991, 266(13): 8531-8539.

Tarasiuk et al., "CSF markers in amyotrophic lateral sclerosis", Journal of Neural Transmission, 2012, 119(7): 747-757.

Turner et al., "Biomarkers in amyotrophic lateral sclerosis", Lancet Neurology, 2009, 8(1): 94-109.

* cited by examiner

AMYOTROPHIC LATERAL SCLEROSIS DIAGNOSTIC COMPOSITION USING ACID SPHINGOMYELINASE, AND METHOD FOR DETECTING DIAGNOSTIC MARKERS

CROSS-REFERENCE TO RELATED APPLICATIONS

This application is a § 371 national phase of International Application No. PCT/KR2017/011665, filed on Oct. 20, 2017, which claims the benefit of Korean Application No. 10-2016-0155859, filed on Nov. 22, 2016, which applications are incorporated by reference herein.

TECHNICAL FIELD

This application claims priority from Korean Patent Application No. 10-2016-0155859 filed on 22 Nov. 2016, the disclosure of which is hereby incorporated in its entirety by reference.

The present invention relates to a composition for diagnosis of amyotrophic lateral sclerosis (ALS) by using acid sphingomyelinase (ASM) and to a detection method for a diagnostic marker and, more specifically, to a method for detecting an ALS marker, the method comprising the steps of: (a) providing a sample of a subject; (b) measuring the expression level or enzymatic activity level of acid sphingomyelinase (ASM) in the sample; (c) determining the subject as having ALS if the expression level or enzymatic activity level of ASM in the subject is increased compared with that of a normal control.

BACKGROUND ART

Amyotrophic lateral sclerosis (ALS) is a neurodegenerative disease caused by degenerative damage of upper motor neurons located in the brain and spinal cord and lower motor neurons. About 10% of ALS cases result from a genetic predisposition, but most occur sporadically. ALS is classified as a rare disease with a prevalence of 2-3 per 100,000 people. The incidence of ALS is about two times higher in males than in females, while sporadic ALS usually occurs at ages of 50-63 years. The causes or progresses of ALS have not been clearly revealed. With respect to the possible causes of ALS, the following hypotheses have been proposed, including: glutamine overproduction resulting in cytotoxicity in motor cells; damaged neurons due to deficiency of nutrients or growth factors necessary to maintain neuronal functions and restore neuronal damage; damaged motor neurons due to viral infection; and the accumulation of substances causing cell death, such as heavy metals and oxidative stress due to environmental pollution, resulting in the death of motor cells. As ALS-causing genes, superoxide dismutase 1 (SOD1), transactive response DNA-binding protein (TARDBP), fused in sarcoma (FUS), chromosome 9 open reading frame 72 (C9orf72), and the like are well known. With the recent discovery of new genes associated with the onset of ALS, this disease has been found to be associated with frontotemporal dementia and various types of muscular diseases and degenerative diseases, and thus has recently been recognized as a disease group of motor neuron diseases.

In the early stage of ALS, degeneration proceeds starting from muscles of hands, fingers, and legs, and muscles become thinner due to reduced muscle mass, which also occurs in the other parts of the body. Patients have difficulty in moving muscles due to muscle rigidity and spasm, and have difficulty in eating since the muscles of the tongue and cheeks becomes gradually weakened. At the end stage of ALS, respiration-related muscles are weakened, increasing the risks of breathing disorder and infection. Meanwhile, the damaged cells in ALS are restricted to motor neurons, while there are thus few disorders in association with biological functions modulated by autonomic nerves, such as peripheral sensation and bladder function, and few intellectual disabilities.

Many studies on ALS were conducted in the 1990s, but there are still few therapies that can stop the progress of ALS or cure ALS. Most of the treatments are symptomatic therapies that prolong the survival period or alleviate symptoms, while drugs showing neuroprotective effects or breathing aids are used. Moreover, the diagnosis of ALS is based on clinical symptoms of motor neuron degeneration, and the progressive pathology of upper and lower motor neurons is mainly checked by patient history and a neurological examination, and nerve conduction tests and electromyography tests are conducted. Many efforts have been made to develop a biomarker for determining a diagnosis and progress rate of ALS and for predicting a prognosis of ALS, but molecular biological indexes of ALS are insufficient.

Therefore, the development of diagnostic reagents and therapeutic agents for ALS is urgent.

DETAILED DESCRIPTION OF THE INVENTION

Technical Problem

The present inventors confirmed that the activity of acid sphingomyelinase, which is important in the sphingolipid metabolism, is increased in plasma and neurons of amyotrophic lateral sclerosis patients, and thus completed the present invention.

Therefore, an aspect of the present invention is to provide a method for detecting a marker of amyotrophic lateral sclerosis (ALS) to provide information necessary for diagnosis of ALS, the method comprising the steps of:
(a) providing a sample of a subject;
(b) measuring the expression level or enzymatic activity level of acid sphingomyelinase (ASM) in the sample; and
(c) determining the subject as having ALS if the expression level or enzymatic activity level of ASM in the subject is increased compared with that of a normal control.

Another aspect of the present invention is to provide a composition for diagnosis of amyotrophic lateral sclerosis, the composition comprising an agent for measuring the enzymatic activity of ASM.

Still another aspect of the present invention is to provide a composition for diagnosis of amyotrophic lateral sclerosis, the composition comprising an agent for measuring the expression level of ASM protein or mRNA.

Still another aspect of the present invention is to provide a use of acid sphingomyelinase (ASM) for preparing an agent for diagnosis of amyotrophic lateral sclerosis (ALS).

Still another aspect of the present invention is to provide a method for diagnosis of amyotrophic lateral sclerosis (ALS), the method comprising the steps of:
(a) providing a sample of a subject;
(b) measuring the expression level or enzymatic activity level of acid sphingomyelinase (ASM) in the sample; and
(c) determining the subject as having ALS if the expression level or enzymatic activity level of ASM in the subject is increased compared with that of a normal control.

Technical Solution

In accordance with an aspect of the present invention, there is provided a method for detecting a marker of amyotrophic lateral sclerosis (ALS) to provide information necessary for diagnosis of ALS, the method comprising the steps of:

(a) providing a sample of a subject;

(b) measuring the expression level or enzymatic activity level of acid sphingomyelinase (ASM) in the sample; and (c) determining the subject as having ALS if the expression level or enzymatic activity level of ASM in the subject is increased compared with that of a normal control.

In accordance with another aspect of the present invention, there is provided a composition for diagnosis of amyotrophic lateral sclerosis, the composition comprising an agent for measuring the enzymatic activity of ASM.

In accordance with another aspect of the present invention, there is provided a composition for diagnosis of amyotrophic lateral sclerosis, the composition consisting of an agent for measuring the enzymatic activity of ASM.

In accordance with another aspect of the present invention, there is provided a composition for diagnosis of amyotrophic lateral sclerosis, the composition consisting essentially of an agent for measuring the enzymatic activity of ASM.

In accordance with still another aspect of the present invention, there is provided a composition for diagnosis of amyotrophic lateral sclerosis, the composition comprising an agent for measuring the expression level of ASM protein or mRNA.

In accordance with still another aspect of the present invention, there is provided a composition for diagnosis of amyotrophic lateral sclerosis, the composition consisting of an agent for measuring the expression level of ASM protein or mRNA.

In accordance with still another aspect of the present invention, there is provided a composition for diagnosis of amyotrophic lateral sclerosis, the composition consisting essentially of an agent for measuring the expression level of ASM protein or mRNA.

In accordance with still another aspect of the present invention, there is provided a use of acid sphingomyelinase (ASM) for preparing an agent for diagnosis of amyotrophic lateral sclerosis (ALS).

In accordance with still another aspect of the present invention, there is provided a method for diagnosis of amyotrophic lateral sclerosis (ALS), the method comprising the steps of:

(a) providing a sample of a subject;

(b) measuring the expression level or enzymatic activity level of acid sphingomyelinase (ASM) in the sample; and (c) determining the subject as having ALS if the expression level or enzymatic activity level of ASM in the subject is increased compared with that of a normal control.

Hereinafter, the present invention will be described in detail.

The present invention provides a method for detecting a marker of amyotrophic lateral sclerosis (ALS) to provide information necessary for diagnosis of ALS, the method comprising the steps of:

(a) providing a sample of a subject;

(b) measuring the expression level or enzymatic activity level of acid sphingomyelinase (ASM) in the sample; and (c) determining the subject as having ALS if the expression level or enzymatic activity level of ASM in the subject is increased compared with that of a normal control.

The term "diagnosis" refers to the determination of the likelihood or onset of a disease, the progression stage of a disease, or the like by checking the presence or characterization of a pathological condition. As used herein, the diagnosis means the determination of the occurrence of amyotrophic lateral sclerosis.

The "amyotrophic lateral sclerosis (ALS)", which is the object of diagnosis in the present invention, is a neurodegenerative disorder, also called Lou Gehrig's disease. Amyotrophic lateral sclerosis is also called a motor neuron disease (MND) since motor neurons of the cerebrum, brain stem, and spinal cord are selectively destroyed. A current method of diagnosing ALS is based on primary clinical symptoms, such as muscle weakness, movement disorders and respiratory disturbance, caused by motor neuron degeneration. A final decision is made by observation of clinical courses after secondary causes of similar clinical diseases are eliminated. Electrophysiologic testing, such as a motor nerve conduction velocity test and electromyography, and histopathological testing of muscles are conducted. The diseases that may show similar symptoms are excluded by conducting cerebrospinal fluid tests, blood tests (serum protein, thyroid hormone, parathyroid hormone, and antibody), urine tests, cervical spine X-ray scans, and MRI scans for excluding the possibility of different diseases accompanying similar symptoms. The mutations of about 20 types of genes have been reported to be associated with the onset of ALS, but genetic ALS cases account for only about 10% of all ALS cases. Moreover, there are limitations in diagnosing ALS through the detection of all gene mutations because of a variety of genes and mutations.

The present invention provides an accurate and efficient biomarker for diagnosing ALS, for which an effective molecular disease diagnostic marker is absent, and a method for detecting a diagnostic marker. The present inventors confirmed that the activity of acid sphingomyelinase (ASM) in the blood and neurons of ALS patients is increased compared with that of a normal control. The present inventors investigated sphingolipid metabolism-related products and enzymatic activity in the blood of healthy controls and the blood of ALS patients having ALS-related genetic mutations, respectively. As a result, the present inventors found that the activity of ASM was consistently increased in the ALS patients, while there was not a great difference in sphingolipid or acid ceramidase activity between the healthy controls and the ALS patients. Also, higher ASM activity was observed in neurons induced from fibroblasts of ALS patients than in induced neurons of a normal control. It may be suggested by the findings of the present inventors that the activity of ASM can be used as a marker for diagnosing ALS by measuring the activity of ASM and detecting a change in the level thereof.

In step (a) in the method of the present invention, a sample of a subject is provided.

The method according to the present invention can be performed without particular limitation on the race, ethnicity, and the like of the subject, while the subject is preferably an Asian, and most preferably a Korean.

ALS cases are greatly divided into two types according to the cause thereof: familial and sporadic (independently occurring). Familial ALS cases account for about 10% of all the ALS cases, and are caused by mutations of one or more genes. It is known that approximately 15% of the ALS familial patients were caused by the mutation of SOD1 gene, and such a disease may occur even when a defective gene is inherited in an autosomal dominant form from one parent. Meanwhile, the cause of sporadic ALS has not been yet specifically revealed. Heavy metals, as environmental factors, such as aluminum, mercury, and lead used in tooth rods, are suggested as causes of the sporadic ALS, which has not yet been proved. In the present invention, ALS patients are not particularly limited to the type thereof, while the subject may have mutations of one or more genes selected form FUS, SOD1, TBK1, C9orf72, TARDBP, OPTN, and NEK1, which are known to be associated with the occurrence of ALS, or sporadic ALS patients.

In an example of the present invention, the present inventors confirmed that as a result of comparison of ASM activity in the blood and neurons between healthy controls and ALS patients with abnormal FUS, SOD1, or TBK1 gene, the ASM activity was consistently increased regardless of the kind of mutant gene of the ALS patients.

SOD1 (superoxide dismutase 1, soluble) is an antioxidant enzyme that eliminates superoxide radicals. The human SOD1 gene is located on chromosome 21q22.11. Approximately 20% of hereditary ALS cases are known to be due to a damage to SOD1 causing oxidative stress, while about 110 kinds of different SOD1 mutations in association with the onset of ALS have been reported. FUS (FUS RNA binding protein/Fused in Sarcoma) is a protein that constitutes heterogeneous nuclear ribonucleoproteins (hnRNP) with various functions, such as transcription activation, splicing, and RNA transport. The human FUS gene is located on chromosome 16p11.2, and about 50 FUS gene mutations have been found in about 5% of the inherited ALS patients. TBK1 (TANK-binding kinase 1) is a protein that activates NFκB in response to a specific cell signal, similar to IκB. The human TBK1 gene is located on chromosome 12q14.1, and is also called FTDALS4 (frontotemporal dementia and/or amyotrophic lateral sclerosis type 4) because of the relevance between frontal dementia and ALS.

The sample of the subject may be selected from the group consisting of skin tissue, nerve tissue, whole blood, plasma, serum, cerebrospinal fluid, urine, saliva, nasal discharge, sputum, bone marrow, amniotic fluid, ascitic fluid, and cervical or vaginal discharge. The nerve tissue may be a tissue of central nerves including brain or peripheral nerves, and may include skin or bone marrow, which is a tissue capable of being induced and differentiated into neurons. In addition, the neurons may be collected or isolated from the subject, or may be neurons induced from non-neuronal cells through, for example, de-differentiation, re-differentiation, cross-differentiation, or differentiation induction.

The sample of the subject may be provided by collection according to a technique known in the art. It is preferable to use a fresh sample to accurately measure the enzyme activity of ASM, while the sample of the subject may be properly pre-treated as known in the art depending on the method of measuring the activity level of ASM to an extent that such pre-treatment does not change the ASM activity level. For example, a sample, such as blood or tissue, may be rapidly frozen using liquid nitrogen and stored frozen at −20° C. or −70° C.

In step (b), the expression level or enzymatic activity level of acid sphingomyelinase (ASM) in the sample collected in the subject is measured.

The "acid sphingomyelinase (ASM)" is a protein belonging to the sphingomyelinase (SMase) family, which is an enzyme that breaks down sphingomyelin into ceramide and phosphorylcholine. The acid sphingomyelinase (ASM) is also called sphingomyelin phosphodiesterase 1 (SMPD1), NPD, aSMase, and the like, and is encoded on the human chromosome 11p15.4-p15.1 by the SMPD1 gene. The mRNA sequence information and the protein sequence information of human ASM are disclosed as NCBI Genbank accession number NM 000543.4 (mRNA) and number NP_000534.3 (protein). The loss of expression or function of ASM results in Niemann-Pick disease, a type of metabolic disease.

SMases are classified on the basis of a pH at which optimum activity thereof is shown, and of the SMases, the activity of ASM is influenced by lipids, cations, pH, redox states, and interactions with other proteins. ASM enzymes are divided into two types, lysosomal sphingomyelinase (L-SMase) and secretory sphingomyelinase (S-SMase) depending on the enzyme location and substrate reactivity. L-SMase is present in cytoplasmic lysosomes, and is considered to be a major enzyme that produces ceramides in response to cell stimulation, such as stress, infection, death signals including a dead ligand, and anticancer drugs. S-SMase is an ASM that is secreted outside cells, and has been reported to mainly break down lipoprotein-linked sphingomyelin into ceramides and coagulate LDL particles. Any ASM for implementing the present invention is applicable so long as it has the characteristics of acid sphingomyelinase regardless of the type of L-SMase or S-SMase.

Any method for measuring the enzymatic activity of ASM can be used without limitation as long as it is commonly used in the art, while ASM activity measurement kits are also commercially available. A method for measuring the enzymatic level of ASM is mainly performed by providing sphingomyelin, a substrate of ASM, at a pH of 4.5-5.0 and measuring the amount of metabolites produced per unit time. For example, the phosphorylcholine produced by ASM activity can be checked by finally measuring the amount of a fluorescent-labeled product through a series of consecutive enzymatic reactions as below: First, the phosphorylcholine is degraded by alkaline phosphatase to choline, and the choline is degraded by choline oxidase to produce $H_2O_2$, which is then finally converted into a fluorescent product, measurable at 530-550 nm, by reactions with horse radish peroxidase and an appropriate substrate (e.g., 10-acetyl-3, 7-dihydroxyphenoxazine). Alternatively, the activity of ASM may be measured through a reaction in which, instead of sphingomyelin, a substrate capable of directly producing a coloring or fluorescent product is provided as a substrate of ASM.

In an example of the present invention, 3 μl of samples were stored at 37° C. in a mixture with an ASM activity buffer. The samples were prepared by stopping a hydrolysis reaction through the addition of 114 μl of ethanol and then carrying out centrifugation. After 30 μl of the prepared samples were transferred into glass vials, 5 μl of the sample was applied to the UPLC system. The ASM concentration levels were measured by comparison with Bodipy(aminoacetaldehyde) combined with sphingomyelin and ceramide.

The enzyme activity measured in a sample may be increased by an improvement in reaction efficiency or reaction rate of an individual enzyme, or by an increase in the number of enzymes. Therefore, when the expression level of ASM measured in the sample of the subject is increased compared with the level of a normal control, it indicates that the level of ASM protein is increased, suggesting that the activity of ASM would also be increased. Accordingly, as a method for predicting ASM activity, the expression level of ASM protein or ASM mRNA may be measured instead of directly measuring ASM activity.

The step of measuring the expression level of ASM may be performed by measuring the expression level of ASM protein or ASM mRNA.

As used herein, the term "polynucleotide" or "nucleic acid" refers to single- or double-stranded deoxyribonucleotide (DNA) or ribonucleotide (RNA). Unless otherwise limited, the polynucleotide or nucleic acid includes known analogs of natural nucleotides that hybridize with nucleic acids in a manner similar to naturally occurring nucleotides. In general, DNA includes four bases, adenine (A), guanine (G), cytosine (C), and thymine (T), while RNA has uracil (U) instead of thymine (T). In the double-stranded nucleic acid, base A forms a hydrogen bond with base T or U, and base C forms a hydrogen bond with base G. Such a relationship between bases is referred to as being "complementary".

Meanwhile, "mRNA (messenger RNA)" is RNA that acts as a blueprint for polypeptide synthesis (or protein translation) by transferring the genetic information of the nucleotide sequence of a particular gene to ribosomes during protein synthesis. Single-stranded mRNA is synthesized through a transcription process using the gene as a template.

As used herein, "protein" is used interchangeably with "polypeptide" or "peptide", and refers to, for example, a polymer of amino acid residues, as typically found in proteins in nature.

As used herein, the term "expression" refers to the formation of a protein or a nucleic acid in cells.

The measurement of mRNA expression can be carried out by using an expression level analysis method, which is common in the art, while examples of the analysis method may include reverse transcription polymerase chain reaction (RT-PCR), competitive RT-PCR, real-time RT-PCR, RNase protection assay (RPA), northern blotting, DNA microarray chip, RNA sequencing, nanostring, or the like, but is not limited thereto.

In addition, the measurement of protein expression levels can be carried out by using a method known in the art without limitation. Examples thereof may include western blotting, dot blotting, enzyme-linked immunosorbent assay, radioimmunoassay (RIA), radial immunodiffusion, Ouchterlony immunodiffusion, rocket immunoelectrophoresis, immunohistochemical staining, immunoprecipitation, complement fixation analysis, flow cytometry (FACS), or a protein chip method, but is not limited thereto.

In step (c), the subject is determined as having ALS if the expression level or enzymatic activity level of ASM measured in step (b) is increased compared with that of a normal control.

If the expression level or activity level of ASM measured in the sample of the subject shows a significant increase compared with that of a normal control, the subject is determined as having ALS. In order to ordinarily investigate whether the expression level or activity level of ASM is changed, the criteria for a normal range is established by measuring the expression levels or activity levels of ASM in samples from a plurality of normal controls. In an example of the present specification, the activity level of ASM measured in the blood (plasma) of normal controls was 0.16-0.17 nmol/ml/h.

Furthermore, the present invention provides a composition for diagnosis of amyotrophic lateral sclerosis, the composition comprising an agent for measuring enzymatic activity of ASM.

The composition for diagnosis according to the present invention may be a composition comprising an agent for measuring enzymatic activity of ASM as an active ingredient, a composition consisting of an agent for measuring enzymatic activity of ASM as an active ingredient, or a composition consisting essentially of an agent for measuring enzymatic activity of ASM as an active ingredient.

As used herein, the term "comprising" is used synonymously with "containing (including)" or "characterized by", and does not exclude specifically unrecited and additional ingredients or method steps in the compositions and methods according to the present invention. The term "consisting of" is meant to exclude additional elements, steps, or ingredients that are not otherwise indicated. The term "consisting essentially of" is meant to include not only described materials or steps but also any material or step that does not substantially affect basic characteristics thereof in the scope of a composition or method.

The agent for measuring the activity of ASM includes a substrate for ASM, such as sphingomyelin, an agent for measuring a reaction product produced by ASM, enzymes, substrates, reaction coenzymes, reaction factors, ions, a standard solution of the reaction product required to derive a standard curve, and the like.

Furthermore, the present invention provides a composition for diagnosis of amyotrophic lateral sclerosis, the composition comprising an agent for measuring the expression level of ASM protein or ASM mRNA.

The composition for diagnosis according to the present invention may be a composition comprising an agent for measuring the expression level of ASM as an active ingredient, a composition consisting of an agent for measuring the expression level of ASM as an active ingredient, or a composition consisting essentially of an agent for measuring the expression level of ASM as an active ingredient.

The agent for measuring the expression level of acid sphingomyelinase (ASM) protein contained in the composition for diagnosis of the present invention may be an antibody specifically binding to ASM protein.

The term "antibody" refers to an immunoglobulin specifically binding to an antigenic region. The antibody in the present invention is an antibody that specifically binds specifically to ASM protein but does not respond to the other proteins including different types of sphingomyelinase other than ASM. A gene encoding ASM is cloned into an expression vector and thus a protein encoded by the gene is obtained, and the ASM antibody may be produced from the obtained protein by a conventional method in the art. The antibody includes a polyclonal antibody or a monoclonal antibody, and includes all the immunoglobulin antibodies that specifically bind to ASM.

In the composition for diagnosis of the present invention, the agent for measuring the expression level of ASM mRNA may be a probe or primer set, which specifically binds to ASM mRNA.

A primer is a short single-stranded oligonucleotide acting as a starting point of DNS synthesis. The primer specifically binds to a polynucleotide as a template under suitable buffer and temperature conditions. DNA is synthesized by allowing DNA polymerase to add and link nucleoside triphosphates having bases complementary to the template DNA to the primer. The primer is generally composed of a sequence of 15-30 nucleotides, and the melting temperature ($T_m$) of the primer for binding to the template strand depends on the nucleotide constitution and length thereof.

A sequence of the primer does not necessarily need to be perfectly complementary to a sequence of some nucleotides in the template, but the primer is appropriate as long as it has sufficient complementarity within a range in which it can perform its inherent actions through the hybridization with the template. Therefore, the primers for measuring the expression level of ASM mRNA in the present invention do not necessarily need to have a sequence perfectly complementary to the ASM gene sequence, while the primers are sufficient as long as they have a length and complementarity for the purpose of measuring the amount of ASM mRNA by amplifying a specific section of ASM mRNA or cDNA through DNS synthesis. The primers for the amplification reaction are composed of a set (pair) of primers that complementarily bind to a template (or sense) and an opposite side (antisense), respectively, of both ends of a specific region of ASM mRNA to be amplified. The primers may be easily designed referring to the nucleotide sequence of ASM mRNA or cDNA by a person skilled in the art.

The term "probe" refers to a fragment of a polynucleotide, such as RNA or DNA, capable of specifically binding to mRNA or complementary DNA (cDNA) of a specific gene and having a length of from several to several hundreds of base pairs. The probe is labeled to check the presence or absence of target mRNA or cDNA to be bound or the expression level thereof. For the purpose of the present invention, the probe complementary to ASM mRNA can be used for the diagnosis of amyotrophic lateral sclerosis by measuring the expression level of ASM mRNA through the hybridization with the sample of the subject. The selection and hybridization conditions of the probe may be properly selected according to the technique known in the art.

The primers or probes of the present invention may be chemically synthesized using phosphoramidite solid support synthesis or other well-known methods. In addition, the primers or probes may be variously modified by a method known in the art to an extent that the hybridization with ASM mRNA is not disturbed. Examples of the modification include methylation, capping, substitution of at least one natural nucleotide with an analogue thereof, and modification between nucleotides, for example, modification with an uncharged linker (e. g., methyl phosphonate, phosphotriester, phosphoroamidate, carbamate, etc) or a charged linker (e. g., phosphorothioate, phosphorodithioate, etc), binding with a labeling material using fluorescence or enzyme, and the like.

Furthermore, the present invention provides a use of acid sphingomyelinase (ASM) for preparing an agent for diagnosis of amyotrophic lateral sclerosis (ALS).

The agent for diagnosis of amyotrophic lateral sclerosis (ALS) may measure the enzymatic activity of ASM.

The agent for diagnosis of amyotrophic lateral sclerosis (ALS) may measure the expression level of ASM protein or ASM mRNA.

Here, a patient having a mutation of at least one gene selected from the group consisting of FUS, SOD1, TBK1, C9orf72, TARDBP, OPTN, and NEK1, or a sporadic ALS patient may be used as a subject for the amyotrophic lateral sclerosis (ALS).

The subject of the present invention may be an animal, preferably a mammal, particularly an animal including a human being, and more preferably a human or a patient in need of diagnosis. The subject is as described above. The subject may be a Korean. In addition, any one selected from the group consisting of skin tissue, nerve tissue, whole blood, plasma, serum, cerebrospinal fluid, urine, saliva, nasal discharge, sputum, bone marrow, amniotic fluid, ascitic fluid, and cervical or vaginal discharge of the subject may be used as a sample.

Furthermore, the present invention provides a method for diagnosis of amyotrophic lateral sclerosis (ALS), the method including:

(a) providing a sample of a subject;
(b) measuring the expression level or enzymatic activity level of acid sphingomyelinase (ASM) in the sample; and
(c) determining the subject as having ALS if the expression level or enzymatic activity level of ASM in the subject is increased compared with that of a normal control.

The expression aspects of ASM are as described above.

Advantageous Effects

Therefore, the present invention provides a method for detecting a diagnostic maker of amyotrophic lateral sclerosis (ALS) by measuring the expression level or enzymatic activity level of acid sphingomyelinase (ASM) in the sample of the subject, and provides a composition therefor. The activity of ASM, among the lipids and enzymes involved in the sphingolipid metabolism, is specifically increased in samples of ALS patients compared with that of a normal control, and thus the activity of ASM can be used as a marker for diagnosing ALS.

MODE FOR CARRYING OUT THE INVENTION

Hereinafter, the present invention will be described in detail.

However, the following examples are merely for illustrating the present invention and are not intended to limit the scope of the present invention.

<Methods>

1. ALS Patient Recruitment and Clinical Trial Protocol Approval

Stem cells were induced using patient skin tissues in sporadic ALS patients and patients with genetic mutations, which meet the diagnosis criteria of ALS based on El Escorial Criteria (revised) among amyotrophic lateral sclerosis patients. Such a method was approved based on the IRB research application No. HYUH 2011-08-010-007 of Hanyang University Hospital.

2. Measurement of Blood Sphingolipids

As for extraction and quantification of the sphingomyelin, ceramide, and sphingosine, the lipids were extracted from a serum sample, and the dried lipid extract was resuspended in 25 µl of 0.2% Igepal CA-630 (Sigma-Aldrich), and respective lipid levels were quantified using the UPLC system.

3. Measurement of ASM and Acid Ceramide (AC) Activity

Several microliters of serum samples and 3 µl of induced neuron samples from ALS patients (FUS, SOD1, TBK1) were mixed with an ASM or AC activity buffer, and stored at 37° C. The samples were prepared by stopping a hydrolysis reaction through the addition of 114 µl of ethanol, followed by centrifugation. After 30 µl of the prepared samples were transferred into glass vials, 5 µl was applied to the UPLC system.

4. Neuron Differentiation

To overcome restrictions of a cell modeling (patient fibroblast) system commonly used in ALS studies, the present study was conducted using patient induced neuron models suitable for neurodegenerative system disorders. The patient induced neurons were obtained by direct conversion by which fibroblasts are converted into functional neurons through the suppression of the polypyrimidine-tract-binding (PTB) protein. The normal controls and patient induced neurons were infected with PTBP1 lentivirus to suppress PTB protein, and after 15 days, enzymatic activity levels were measured.

Example 1

Measurement of Sphingolipid Levels in Blood

In order to investigate the effect of amyotrophic lateral sclerosis (ALS) on the sphingolipid metabolism, sphingolipid levels in blood of healthy controls and patients diagnosed with ALS were measured and compared. The patients diagnosed with ALS were confirmed to have mutations of any one gene of FUS (p.Q519E, p.G504Wfs*12, p.R495*), SOD1 (p.I105T, p.G11V), and TBK1 (p.I472Sfs*8, I475T, R384W).

Figure 2:
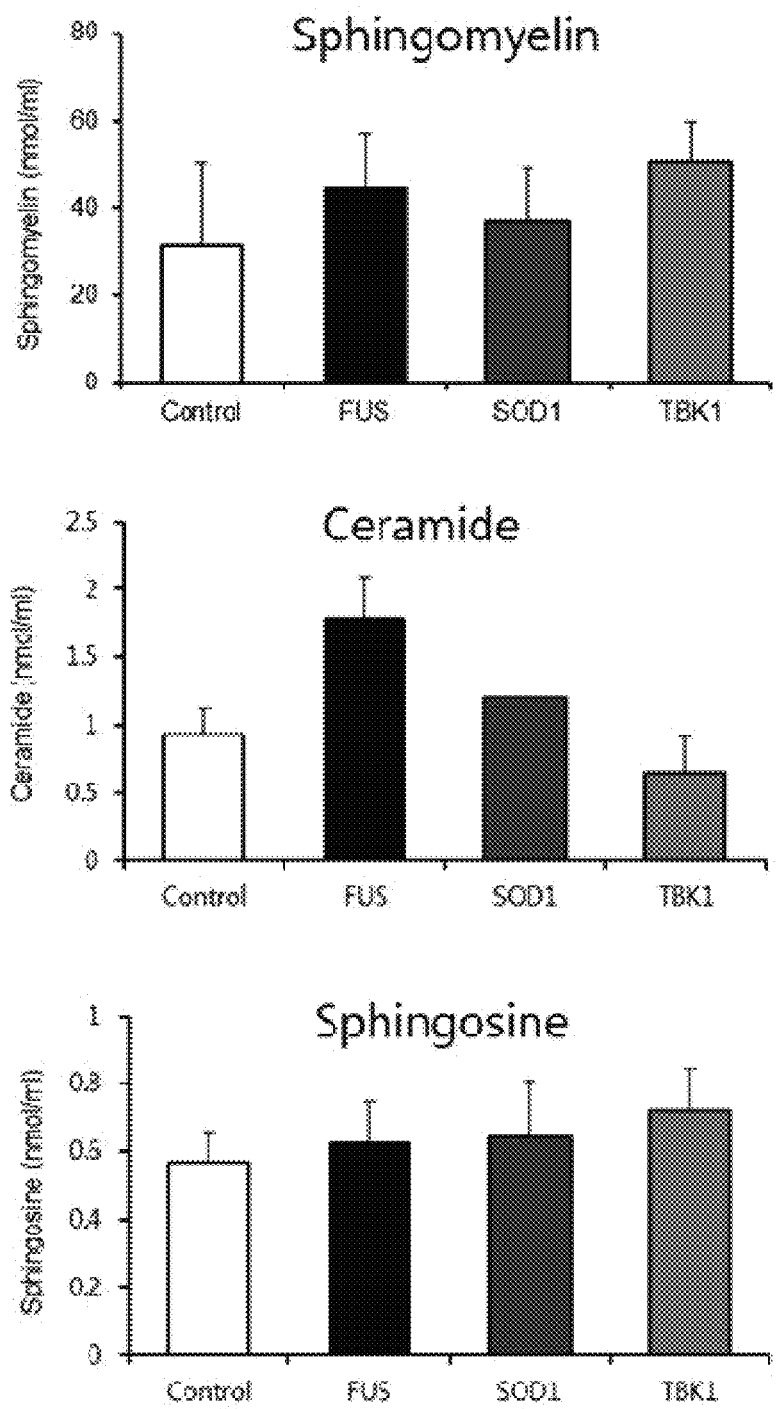
FIG. 2 shows the levels of sphingomyelin, ceramide, and sphingosine, measured in the plasma of normal controls and ALS patients (FUS, SOD1, TBK1).

As can be seen from FIG. 2, no consistent differences were observed between normal controls and ALS patients in view of the levels of analysis target sphingolipids, including sphingomyelin, ceramide, and sphingosine, measured in plasma. There were no significant differences in the levels of sphingomyelin and sphingosine in blood between normal controls and ALS patients. In the case of ceramide, ALS patients with FUS gene mutations showed relatively high levels compared with normal controls, while there was no significant difference among all the ALS patients. No significant changes were shown in the levels of sphingolipids in blood between healthy controls and ALS patients.

Example 2

Measurement of Acid Sphingomyelinase and Acid Ceramidase Activity in Blood

In order to investigate the effect of amyotrophic lateral sclerosis (ALS) on the sphingolipid metabolism, the activity levels of sphingolipid-related enzymes in blood of healthy controls and patients diagnosed with ALS were measured and compared.

Figure 1:
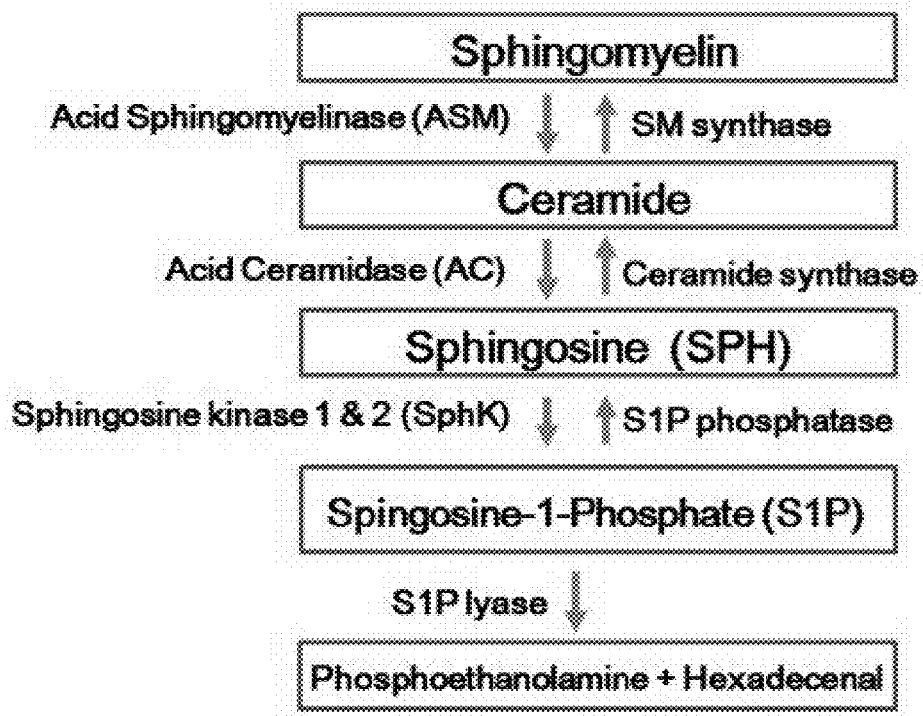
FIG. 1 is a schematic diagram showing enzymes involved in a sphingolipid metabolism.

The activity of sphingolipid-related enzymes, i.e., acid sphingomyelinase (ASM) that breaks down sphingomyelin into ceramide and phosphorylcholine and acid ceramidase (AC) that breaks down ceramide into sphingosine and fatty acid, was measured. The sphingolipid metabolism and main enzymes involved therein are shown in FIG. 1.

Figure 3:
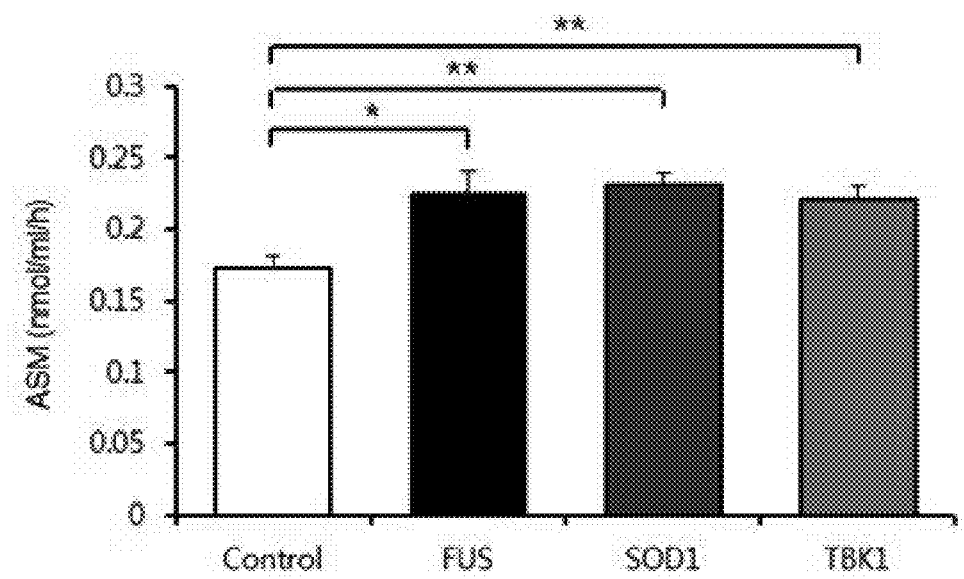
FIG. 3 shows the activity levels of acid sphingomyelinase and acid ceramidase measured in the plasma of normal controls and ALS patients (FUS, SOD1, TBK1). The marks * and ** indicate a statistically significant difference, respectively.
Figure 3:
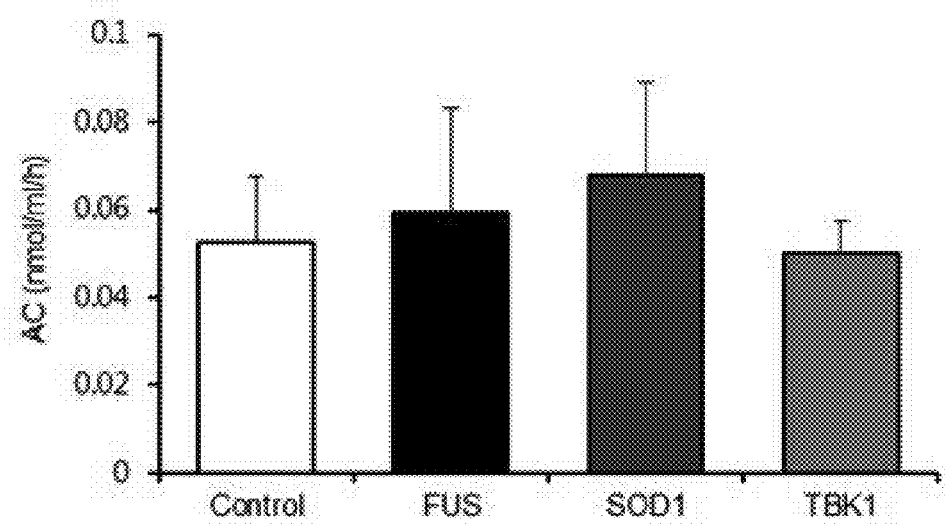

As can be seen from FIG. 3, it was found that the ASM activity measured in plasma was increased in all the ALS patient groups compared with normal controls. The ASM activity in the ALS patient groups showed consistent and statistically significant differences compared with normal controls, regardless of the type of ALS-related gene. In contrast, the AC activity measured in plasma showed no significant difference between normal controls and ALS patient groups. There was no difference in sphingolipids and the activity level of AC between normal controls and ALS patients, but the activity level of ASM was specifically significantly increased in ALS patients, indicating that the activity level of ASM can be used as a marker for diagnosing ALS.

Example 3

Measurement of Acid Sphingomyelinase Activity in Induced Neurons

It was investigated whether an increase in ASM activity confirmed in blood of ALS patients was also observed in induced neurons. Fibroblasts collected from healthy controls and ALS patients were allowed to differentiate into neurons, and the activity of ASM was investigated in the differentiated (induced) neurons.

Figure 4:
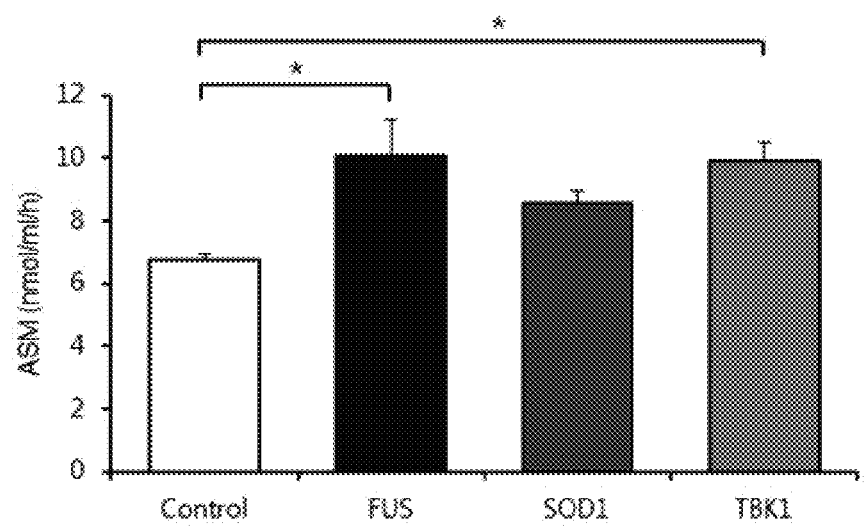
FIG. 4 shows the enzymatic activity level of acid sphingomyelinase measured in induced neurons from normal controls and ALS patients (FUS, SOD1, TBK1), respectively. The mark indicates a statistically significant difference.

As shown in FIG. 4, the activity of ASM was measured to be higher in the induced neurons from the ALS patients than in those from the normal controls, and thus showed similar changes to those observed in plasma. These results suggest that the activity level of ASM can be used as a marker for diagnosing ALS through the measurement of a change in the activity level of ASM.

INDUSTRIAL APPLICABILITY

The compositions and methods according to the present invention can facilitate the development of novel and effective diagnostic reagents capable of easily diagnosing amyotrophic lateral sclerosis.

The invention claimed is:

1. A method for treating amyotrophic lateral sclerosis (ALS), comprising:
    (a) measuring the level or activity of acid sphingomyelinase (ASM) in a sample of serum or plasma from a subject; and
    (b) identifying the subject as having increased ASM compared with that of a normal control subject; and
    (c) administering a treatment for amyotrophic lateral sclerosis to the subject.

2. The method of claim 1, wherein the subject is a patient having a mutation of at least one gene selected from the group consisting of FUS, SOD1, TBK1, C9orf72, TARDBP, OPTN, and NEK1, or a sporadic ALS patient.

3. The method of claim 1, wherein step (a) is done by measuring the amount of ASM protein in the sample.

4. The method of claim 1, wherein step (a) is done by an ASM activity assay.

5. The method of claim 1, wherein step (a) does not comprise measuring sphingomyelin ceramide and sphingosine in the sample.

* * * * *